United States Patent [19]

Keith et al.

[11] Patent Number: 4,472,372
[45] Date of Patent: Sep. 18, 1984

[54] POLYMERIC DIFFUSION MATRIX CONTAINING CHLORPHENIRAMINE MALEATE

[75] Inventors: Alec D. Keith, Miami, Fla.; Wallace Snipes, State College, Pa.

[73] Assignee: Key Pharmaceuticals, Inc., Miami, Fla.

[21] Appl. No.: 425,274

[22] Filed: Sep. 28, 1982

Related U.S. Application Data

[63] Continuation of Ser. No. 291,474, Aug. 10, 1981, abandoned, which is a continuation of Ser. No. 167,008, Jul. 9, 1980, abandoned, which is a continuation-in-part of Ser. No. 109,242, Jan. 3, 1980, abandoned, which is a continuation-in-part of Ser. No. 2,565, Jan. 11, 1979, abandoned, and Ser. No. 47,084, Jun. 11, 1979, abandoned.

[30] Foreign Application Priority Data

Aug. 14, 1979 [JP] Japan ................................ 54-103459

[51] Int. Cl.$^3$ ...................... A61L 15/03; A61F 13/00; A61K 9/70
[52] U.S. Cl. ........................................ 424/19; 424/22; 424/28; 424/78; 424/80
[58] Field of Search .............................. 424/28, 78, 80

[56] References Cited

FOREIGN PATENT DOCUMENTS

1465665  2/1977  United Kingdom .

OTHER PUBLICATIONS

The Pharmacological Basis of Therapeutics, L. S. Goodman and A. Gilman, pp. 603–610, (1975).
Kamishita et al., Chem. Abstr. 85, #254116 (1976) of Japan, Kokai 76 44618, Apr. 16, 1976.
Stephenson et al., Chem. Abstr. 46, #11449 & (1952) Local Anesthetic Potency of Twenty Antihistamines in Guinea Pigs by the Intralutaneous Wheal Method.
Steffen et al., CA. 53, #15348e (1959), Evaluation of Various Antihistamines as Local Anesthetic Agents.
Kushima et al., CA. 62, #12977e, (1965), Lidocaine in Hydrophalic Ointment Conte Chlorpheniramine Maleate.
Hattori et al., CA. 21, #78963, (1979), Dexamethasone and Chlorpheniramine Maleate in Ointment.

*Primary Examiner*—Shep K. Rose
*Attorney, Agent, or Firm*—Wegner & Bretschneider

[57] ABSTRACT

There is disclosed a polymeric diffusion matrix for the sustained release of chlorpheniramine maleate by transdermal delivery to a patient wherein the matrix comprises a polar plasticizer, polyvinylalcohol, polyvinylpyrrolidone, and a pharmaceutically effective amount of chlorpheniramine maleate.

4 Claims, No Drawings

POLYMERIC DIFFUSION MATRIX CONTAINING CHLORPHENIRAMINE MALEATE

CROSS-REFERENCE TO RELATED APPLICATIONS

This application is a continuation application of U.S. application Ser. No. 291,474, filed Aug. 10, 1981, now abandoned, which in turn is a continuation of U.S. application Ser. No. 167,008, filed July 9, 1980, now abandoned, which in turn is a continuation-in-part of U.S. application Ser. No. 109,242, filed Jan. 3, 1980, now abandoned, which in turn is a continuation-in-part of U.S. application Ser. No. 2,565, filed Jan. 11, 1979, now abandoned, and Ser. No. 47,084, filed June 11, 1979, now abandoned.

SUMMARY OF THE INVENTION

The present invention relates to a polymeric diffusion matrix containing chlorpheniramine maleate. More particularly, the invention relates to a polymeric diffusion matrix containing chlorpheniramine maleate characterized by a sustained release of chlorpheniramine maleate.

A self-supporting polymeric diffusion matrix is provided for the sustained release of chlorpheniramine maleate in order to transdermally deliver said chlorpheniramine maleate to a patient and provide said patient with an antihistamine effect, said matrix comprising from about 2 to about 60% by weight of a polar plasticizer; from about 6 to about 20% by weight polyvinylalcohol; from about 2 to about 10% by weight polyvinylpyrrolidone; and a pharmaceutically effective amount of chlorpheniramine maleate to provide a sustained release of said chlorpheniramine maleate over a prolonged period.

In one embodiment the polar plasticizer is glycerol present in an amount of from about 2 to about 60% by weight. In another embodiment the polar plasticizer is polyethylene glycol present in an amount of from about 2 to about 15% by weight. A still further embodiment contemplates a mixture of glycerol and polyethylene glycol wherein the latter is present in an amount by weight of from about 1 to about 5 parts per weight glycerol.

The self-supporting polymeric diffusion matrix generally contains a mixture of polyvinylalcohol and polyvinylpyrrolidone, although it will be understood that other polymeric mixtures may be used provided they yield the desired sustained release effect. For example, both the polyvinylalcohol and the polyvinylpyrrolidone may be completely replaced with from about 1 to about 9% agar or agarose, and preferably from about 1.5 to 3% agar or agarose, 2% agar or agarose being particularly preferred.

As the polyvinylalcohol used in the present invention there is generally contemplated one having a molecular weight from about 50,000 to about 150,000, and more preferably about 100,000 to about 150,000, 115,000 having been used in related systems of the present inventors with success. The polyvinylalcohol should be hydrolyzed, generally at least to the extent of 90%, with a preferred embodiment being at least 95% hydrolyzed. Polyvinylpyrrolidone should have a molecular weight of from about 15,000 to about 85,000, and more preferably from about 20,000 to about 60,000. Polyvinylpyrrolidone with a molecular weight of 40,000 is a particularly preferred embodiment.

The amount by weight of the ingredients other than the polar plasticizer generally should be in the following ranges: polyvinylalcohol is generally present in an amount of from about 6 to about 20% by weight, with 10% being a preferred embodiment; polyvinylpyrrolidone is present generally in an amount of from about 2 to about 10% by weight.

The amount of the chlorpheniramine maleate to be delivered by day is generally about 1 to about 30 mg, preferably about 3 mg, which is generally lower than the oral dosage. This is accounted for due to the fact that in oral applications much of the chlorpheniramine maleate can be expected to be lost by the first pass through the liver. To assure that the desired quantity of chlorpheniramine maleate is delivered, an excess of the drug should be incorporated in the matrix.

The water-soluble polymer can be replaced with (in addition to agar) gum arabic, gum tragacanth, polyacrylic acid, polymethacrylic acid, polyvinyloxazolidone, polyvinylmorpholinone, and polyvinylpiperidone.

Polyalkylene glycols such as polyethylene glycol and polypropylene glycol may replace all or part of the glycerol.

It is possible to replace the polyvinylalcohol with polymers of hydroxyethylacrylate, polymers of hydroxyethylmethacrylate, polymers of hydroxypropylacrylate, and polymers of hydroxypropylmethacrylate.

It will be appreciated that chlorpheniramine maleate may be added to the above mixture not only in the form of the pure chemical compound, but also in admixture with other drugs that may be transdermally applied or with other ingredients which are not incompatible with the desired objective of transdermally administering the drug to a patient. Thus, simple pharmacologically acceptable derivatives of the drugs such as ethers, esters, amides, acetals, salts, and the like may be used. With some drugs such derivatives may actually be preferred.

In forming the matrix, excess water is not required. In accordance with a preferred aspect of the present invention, about 2% by weight chlorpheniramine maleate is included in the diffusion matrix. The resultant homogeneous mixture is poured into forms preferably made of glass or stainless steel, these forms or templates producing a diffusion matrix having a thickness of about 1 to about 3 mm in accordance with a preferred aspect of the present invention. This diffusion matrix is either cast or cut into pieces of the desired size.

The following methods may be used for preparing the diffusion matrix of the present invention.

In a first method, the matrix is formed at atmospheric pressure. Water and glycerol are first mixed together.

A polar plasticizer such a glycerol is a necessary component in the matrix. A matrix formed without a polar plasticizer is not flexible and has poor diffusional contact with the skin causing unreliable diffusion release.

The polyvinylalcohol and polyvinylpyrrolidone are then added to the polar plasticizer-water mixture at room temperature, with agitation. The mixture is heated to a temperature within the range of from about 90° to about 95° C. at atmospheric pressure to extend the polymers. If desired, the mixture may be maintained at an elevated temperature for a period of time, based on polymer stability, prior to addition of the drug. Thus, the mixture is stable for a period of time and may be kept for such a period before being mixed with the drug to be delivered to the patient. Thereafter, the mixture is temperature-adjusted and the drug to be applied to the patient is then added to the mixture, with thorough agitation. Once a homogeneous mixture of the polymer solution and drug is obtained, the mixture is ready to be cast to form in a drug-containing diffusion matrix. After casting the mixture is cooled to a temperature such that gelation occurs. In a preferred embodiment, the drug may be dissolved by agitation in a suitable solvent such as glycerin and water. The thus-obtained solution can be maintained at room temperature for prolonged periods without deterioration.

It has been found that curing is facilitated by subjecting the matrix to a temperature down to about −20° C. immediately after casting. The setting period is quickened considerably.

Sodium dodecyl sulfate or sorbitan (Tween-20) or other detergents may be added in an amount of 0.1 to 10% by weight, based on the matrix, as a dispersing agent, if desired.

An absorption facilitator to insure skin penetration such as dimethylsulfoxide, decylmethylsulfoxide, or other penetration enhancers may be added.

The present drug delivery device comprises the drug-containing diffusion matrix and means for fastening the matrix to the skin of a patient. Such means can take various forms, such as an occlusive backing layer forming a kind of "bandage" with the diffusion matrix being held against the skin of a patient being treated. A polyethylene or Mylar tape is contemplated as one form of occlusive layer in accordance with the present invention. It can also take the form of an elastic band, such as a cloth band, a rubbery band or other material. Here, the diffusion matrix is placed directly on the skin and held in place by such elastic band which typically will be placed over the arm or wrist of the patient. An intermediate adhesive layer between the diffusion matrix and the skin capable of permitting the transdermal application of the drug can also be used.

The invention is illustrated by the following non-limiting Examples:

EXAMPLE I

Together there are mixed 30 gm glycerol and 45 ml water. This mixture is heated to 90° C.; after reaching at least 70° C. there are slowly added 15 gm polyvinylalcohol (PVA 100% hydrolyzed, molecular weight 115,000) and 8 gm polyvinylpyrrolidone (mw 40,000). The mixture is stirred at 90° C. until solution is effected, which may take about 10 minutes; it will be appreciated that with larger quantities, a considerably longer period of time may be needed. 98 ml of this solution is then mixed with 2 g chlorpheniramine maleate, this mixture then being mechanically stirred until homogeneous. The homogeneous mixture is then poured into forms made of glass or stainless steel which serve as templates to produce a diffusion matrix having a thickness of about 2 to 3 mm. This diffusion matrix is then cut into pieces with a total surface area suitable for the administration of a pharmaceutically effective amount of chlorpheniramine maleate.

The diffusion matrix is applied to the skin of a patient in need of an antihistamine effect, the chlorpheniramine maleate being transdermally delivered to the skin of the patient. The diffusion matrix is ideally applied to the skin of the patient by means of a single-piece bandage having the diffusion matrix in the center under the occlusive layer, the bandage being provided to the patient with a peel-of cover much like a "band-aid".

EXAMPLE II

In place of the glycerol of Example I, there is substituted 5 gm polyethylene glycol having a molecular weight of 1000 and 25 ml water. The resultant diffusion matrix is more rigid than that of Example I.

EXAMPLE III

In place of the glycerol of Example I, there is substituted 5 gm polyethylene glycol (mw 1,000), 4 gm glycerol and 21 ml water. The resultant diffusion matrix shares the improved rigidity of the diffusion matrix of Example II, while providing contact with the skin characteristic of the glycerol in this type of diffusion matrix.

EXAMPLE IV

In place of the polyvinylalcohol and polyvinyl pyrrolidone of Example I, there is substituted 2% by weight agarose, yielding a diffusion matrix for the transdermal delivery of chlorpheniramine maleate.

What is claimed is:

1. In a method for the administration of chlorpheniramine maleate to a patient to provide said patient with an antihistamine effect, the improvement comprising applying to the skin of said patient a self-supporting diffusion matrix made by casting or molding and comprising from about 2 to about 60% by weight of a polar plasticizer, from about 6 to about 20% by weight of polyvinylalcohol molecular weight of about 50,000 to about 150,000, from about 2 to about 10% by weight polyvinylpyrrolidone molecular weight of from about 15,000 to about 85,000, and a pharmaceutically effective amount of chlorpheniramine maleate to transdermally deliver and provide a sustained release of said chlorpheniramine maleate over a prolonged period.

2. The method of claim 1 wherein said chlorpheniramine maleate is present in an amount to provide sustained release of about 1 to about 30 mg per day.

3. The polymeric diffusion matrix of claim 1 wherein said polar plasticizer is glycerol.

4. The polymeric diffusion matrix of claim 1 wherein said polyvinylpyrrolidone has a molecular weight of about 20,000 to about 60,000.

* * * * *